(12) United States Patent
Fernald et al.

(10) Patent No.: US 8,100,901 B2
(45) Date of Patent: *Jan. 24, 2012

(54) ABLATION PROBE WITH ECHOGENIC INSULATIVE SHEATH

(75) Inventors: Kathleen Fernald, Brookline, MA (US); Robert F. Rioux, Ashland, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/878,794

(22) Filed: Sep. 9, 2010

(65) Prior Publication Data

US 2011/0009862 A1 Jan. 13, 2011

Related U.S. Application Data

(63) Continuation of application No. 11/456,034, filed on Jul. 6, 2006, now Pat. No. 7,799,022.

(51) Int. Cl.
*A61B 18/18* (2006.01)

(52) U.S. Cl. .......................... 606/41; 600/458; 600/459

(58) Field of Classification Search .............. 606/41–45
See application file for complete search history.

(56) References Cited

U.S. PATENT DOCUMENTS

| | | | |
|---|---|---|---|
| 5,081,997 | A | 1/1992 | Bosley, Jr. et al. |
| 5,201,314 | A | 4/1993 | Bosley, Jr. et al. |
| 5,289,831 | A | 3/1994 | Bosley |
| 5,921,933 | A | 7/1999 | Sarkis et al. |
| 6,106,473 | A | 8/2000 | Violante et al. |
| 6,379,353 | B1 | 4/2002 | Nichols |
| 6,506,156 | B1 | 1/2003 | Jones et al. |
| 2002/0151796 | A1 | 10/2002 | Koulik |
| 2003/0212394 | A1 | 11/2003 | Pearson et al. |
| 2004/0077948 | A1 | 4/2004 | Violante et al. |
| 2004/0162554 | A1 | 8/2004 | Lee et al. |
| 2004/0167509 | A1 | 8/2004 | Taimisto |
| 2004/0181216 | A1 | 9/2004 | Kelly et al. |
| 2008/0009852 | A1 | 1/2008 | Fernald et al. |
| 2008/0041901 | A1 | 2/2008 | Chuang |

FOREIGN PATENT DOCUMENTS

| | | |
|---|---|---|
| EP | 0552924 A1 | 7/1993 |
| EP | 1118337 A2 | 7/2001 |
| EP | 1118337 A3 | 1/2002 |

OTHER PUBLICATIONS

PCT International Search Report for PCT/US2007/071124, Applicant: Boston Scientific Scimed, Inc., Form PCT/ISA/210 and 220, dated Sep. 11, 2007 (6 pages).
PCT Written Opinion of the International Search Authority for PCT/US2007/071124, Applicant: Boston Scientific Scimed, Inc., Form PCT/ISA/237, dated Sep. 11, 2007 (5 pages).
PCT International Preliminary Report on Patentability (Chapter I of the Patent Cooperation Treaty) for PCT/US2007/071124, Applicant: Boston Scientific Scimed, Inc., Form PCT/IB/326 and 373, dated Jan. 15, 2009 (7 pages).

*Primary Examiner* — Linda Dvorak
*Assistant Examiner* — Amanda Scott
(74) *Attorney, Agent, or Firm* — Vista IP Law Group LLP

(57) ABSTRACT

Tissue ablation probes are provided. Each tissue ablation probe comprises an electrically conductive probe shaft, at least one tissue ablation electrode carried by a distal end of the probe shaft, and an electrically insulative outer sheath disposed on the probe shaft. The sheath is at least partially composed of polyether ether ketone (PEEK) and another material comprising condensed-phase particles interspersed throughout the PEEK to increase the echogenicity of the outer sheath. The durability of the PEEK allows the sheath to be formed as thinly as possible, thereby minimizing the diameter of the ablation probe, while the inclusion of condensed-phase particles within the PEEK does not significantly degrade the durability of the sheath.

20 Claims, 5 Drawing Sheets

ABLATION PROBE WITH ECHOGENIC INSULATIVE SHEATH

CROSS REFERENCE TO RELATED APPLICATIONS

This application is a continuation of U.S. patent application Ser. No. 11/456,034, now allowed, filed Jul. 6, 2006. The above-noted Application is incorporated by reference as if set forth fully herein.

FIELD OF THE INVENTION

The field of the invention relates generally to the structure and use of radio frequency (RF) ablation probes for the treatment of tissue.

BACKGROUND OF THE INVENTION

The delivery of radio frequency (RF) energy to target regions within solid tissue is known for a variety of purposes of particular interest to the present invention. In one particular application, RF energy may be delivered to diseased regions (e.g., tumors) for the purpose of ablating predictable volumes of tissue with minimal patient trauma.

RF ablation of tumors is currently performed using one of two core technologies. The first technology uses a single needle electrode, which when attached to a RF generator, emits RF energy from an exposed, uninsulated portion of the electrode. The second technology utilizes multiple needle electrodes, which have been designed for the treatment and necrosis of tumors in the liver and other solid tissues. U.S. Pat. No. 6,379,353 discloses such a probe, referred to as a LeVeen Needle Electrode™, which comprises a cannula and an electrode deployment member reciprocatably mounted within the delivery cannula to alternately deploy an electrode array from the cannula and retract the electrode array within the cannula. Using either of the two technologies, the energy that is conveyed from the electrode(s) translates into ion agitation, which is converted into heat and induces cellular death via coagulation necrosis. The ablation probes of both technologies are typically designed to be percutaneously introduced into a patient in order to ablate the target tissue.

In the design of such ablation probes, which may be applicable to either of the two technologies, RF energy is often delivered to an electrode located on a distal end of the probe's shaft via the shaft itself. This delivery of RF energy requires the probe to be electrically insulated to prevent undesirable ablation of healthy tissue. In the case of a single needle electrode, all but the distal tip of the electrode is coated with an electrically insulative material in order to focus the RF energy at the target tissue located adjacent the distal tip of the probe. In the case of a LeVeen Needle Electrode™, RF energy is conveyed to the needle electrodes through the inner electrode deployment member, and the outer cannula is coated with the electrically insulative material to prevent RF energy from being transversely conveyed from the inner electrode deployment member along the length of the probe.

The procedure for using the ablation probe requires the insulative coating to have sufficient durability. To illustrate, when designing RF ablation probes, it is desirable to make the profile of the probe shaft as small as possible, namely to have a smaller gauge size, in order to minimize any pain and tissue trauma resulting from the percutaneous insertion of the probe into the patient. Thus, it is advantageous for the electrically insulative material applied to the probes be as thin as possible. However, RF ablation probes are often introduced through other tightly toleranced devices that may compromise the integrity of the thinly layered insulation, thereby inadvertently exposing healthy tissue to RF energy.

For example, probe guides are often used to point ablation probes towards the target tissue within a patient. A typical probe guide takes the form of a rigid cylindrical shaft (about 1-2 inches in length) that is affixed relative to and outside of a patient, and includes a lumen through which the ablation probe is delivered to the target tissue. To maximize the accuracy of the probe alignment, it is desirable that the guide lumen through which the probe is introduced be about the same size as the outer diameter of the probe, thereby creating a tight tolerance between the probe and the probe guide. As another example, ablation probes are also often used with co-access assemblies that allow several different devices, such as ablation probes, biopsy stylets, and drug delivery devices, to be serially exchanged through a single delivery cannula. To minimize pain and tissue trauma, it is desirable that the profile of the delivery cannula be as small as possible. To achieve this, the lumen of the delivery cannula will typically be the same size as the outer diameter of the ablation probe, thereby creating a tight tolerance between the probe and the delivery cannula.

As a result, during the initial introduction of the probe through a delivery device, such as a probe guide or cannula of a co-access system, it is possible that a portion of the insulation may shear off as the probe is introduced through the delivery device. Consequently, the attending physician will either have to replace the probe with a new one or risk ablating healthy tissue. Thus, the durability of the insulative coating is critical to prevent damaging healthy tissue and/or having to discard the probe.

Besides providing the insulation on the ablation probe with the necessary durability, it is also necessary to ensure that the distal end of the ablation probe, where the RF energy will be directed, is in contact with the target tissue. This may be achieved with an imaging device located outside the patient's body, such as an ultrasound imager. The echogenicity of the probe determines how well the probe may be located using ultrasound techniques. That is, the more echogenetic the ablation probe, the easier it is to determine the location of the probe with ultrasound imaging and to ensure accurate contact with the target tissue.

To achieve greater echogenicity, it is known in the art, for example, to make marks or nicks along the shaft in order to increase the amount of edges and surfaces on the shaft, thereby creating a non-uniform surface profile. Echogenicity increases as the number of edges and surfaces for reflecting the ultrasound is increased. This technique may also be applied to insulative coating on the probe shaft. It is also known in the art to have air bubbles interspersed throughout the insulative coating in order to increase echgenicity. However, the inclusion of air bubbles may degrade the integrity of the insulative coating, which may also occur when marks or nicks are made in the insulative coating.

Therefore, there is a need in the art for an ablation probe with an insulative coating having improved echogenicity for properly positioning the ablation device relative to the target tissue, while also having sufficient durability and size to remain intact during insertion and use of the ablation probe.

SUMMARY OF THE INVENTION

In accordance with the present inventions, tissue ablation probes are provided. Each tissue ablation probe comprises an electrically conductive probe shaft, at least one tissue ablation electrode carried by a distal end of the probe shaft, and an electrically insulative outer sheath disposed on the probe shaft. The ablation probe may, e.g., be affixed to, or deployable from, the distal end of the probe shaft. In one embodiment, the outer sheath is fixably disposed on the probe shaft, although in other embodiments, the outer sheath may be slidably disposed on the probe shaft. The ablation probe may further comprise an electrical connector carried by a proximal end of the probe shaft, wherein the electrical connector is electrically coupled to the tissue ablation electrode(s) through the probe shaft. In accordance with the present inventions, a method of ablating tissue comprises introducing the tissue ablation probe through a delivery device into a tissue region (e.g., percutaneously), and ablating the tissue region with the at least one tissue ablation electrode.

In accordance with a first aspect of the present inventions, the sheath is at least partially composed of a polyether ether ketone (PEEK). Although the present inventions should not be so limited in their broadest aspects, the durability of the PEEK allows the sheath to be formed as thinly as possible, thereby minimizing the diameter of the ablation probe. In an optional embodiment, tissue ablation probe may further comprise particles distributed through the PEEK to increase the echogenicity of the tissue ablation probe. In one embodiment, the particles are solid, so that the durability of the sheath is not degraded. However, because the PEEK provides the sheath with maximum durability, in some embodiments, the particles may be gel or liquid particles, and even gas particles, without significantly degrading the durability of the sheath.

In accordance with a second aspect of the present inventions, the sheath is at least partially composed of a base material and another material interspersed throughout the base material to increase the echogenicity of the outer sheath. The other material comprises condensed-phase particles (such as, solid particles, gel particles, or liquid particles). While the present inventions should not be so limited in their broadest aspects, the use of condensed-phase particles may ensure that the durability of the outer sheath is not significantly degraded even if a conventional insulative material (e.g., a non-PEEK material) is used as the base material. The other material may optionally be interspersed in non-uniform portions and/or non-uniform locations in the base material. The other material may also be composed of more than one substance if desired.

In accordance with a third aspect of the present inventions, the sheath is at least partially composed of polyether ether ketone (PEEK) and another material comprising condensed-phase particles interspersed throughout the PEEK to increase the echogenicity of the outer sheath. Although the present inventions should not be so limited in their broadest aspects, the durability of the PEEK allows the sheath to be formed as thinly as possible, thereby minimizing the diameter of the ablation probe, while the inclusion of condensed-phase particles within the PEEK does not significantly degrade the durability of the sheath.

Other and further aspects and features of the invention will be evident from reading the following detailed description of the preferred embodiments, which are intended to illustrate, not limit, the present inventions.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE EMBODIMENTS

Figure 1:
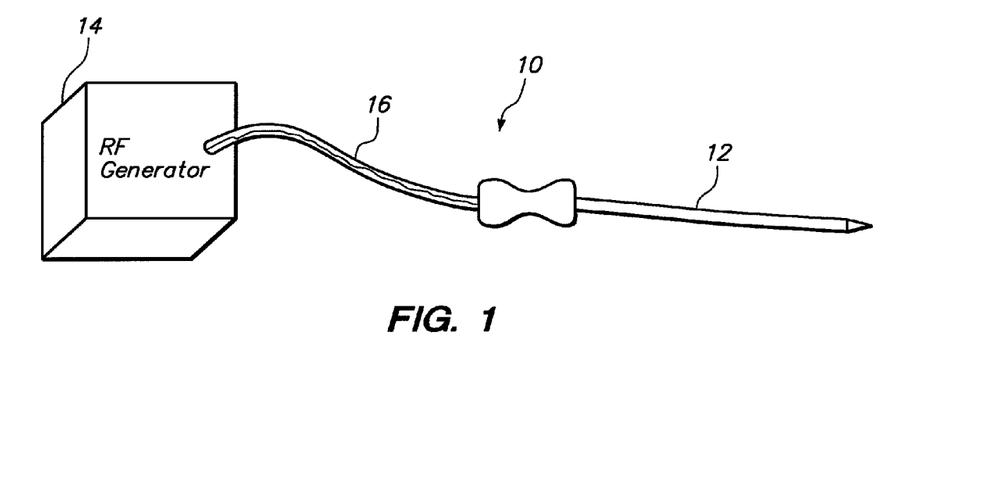
FIG. 1 is a plan view of a tissue ablation system arranged in accordance with one embodiment of the present inventions.

Referring to FIG. 1, a tissue ablation system 10 constructed in accordance with one embodiment of the present inventions, will now be described. The tissue ablation system 10 generally comprises an ablation probe 12 configured for introduction into the body of a patient for ablative treatment of target tissue, a source of ablation energy, and in particular a radio frequency (RF) generator 14, and a cable 16 electrically connecting the ablation probe 12 to the RF generator 14.

Figure 2:
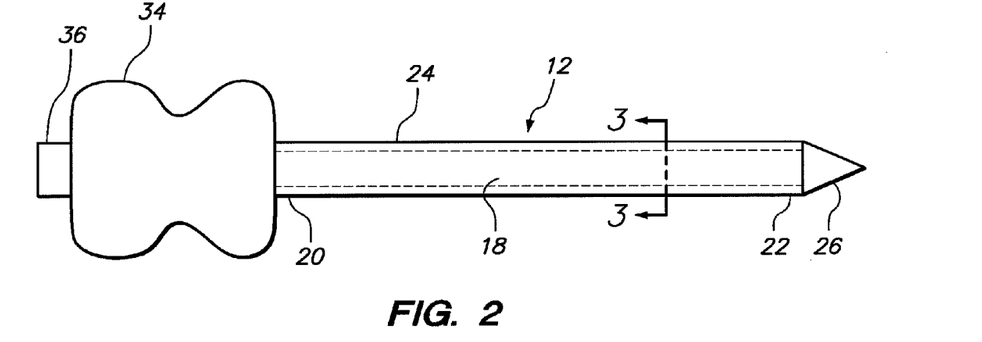
FIG. 2 is a side view of a tissue ablation probe used in the tissue ablation system of FIG. 1.

Referring now to FIG. 2, the ablation probe 12 will be described in further detail. The ablation probe 12 comprises an elongated, probe shaft 18 having a proximal end 20 and a distal end 22. The probe shaft 18 is composed of an electrically conductive material, such as stainless steel. The probe shaft 18 has a suitable length, typically in the range from 5 cm to 30 cm, preferably from 10 cm to 25 cm, and an outer diameter consistent with its intended use, typically being from 0.7 mm to 5 mm, usually from 1 mm to 4 mm.

The ablation probe 12 further comprises an electrically insulative outer sheath 24 disposed on the probe shaft 18. In the illustrated embodiment, the sheath 24 is affixed to the probe shaft 18, and may be applied to the probe shaft 18 using any suitable means. For example, the insulative outer sheath 24 can be applied to the probe shaft 18 as a heat shrink or can be extruded onto the probe shaft 18.

The sheath 24 is composed of a base material 50 that is electrically insulative with sufficient durability to be inserted into a probe guide. One preferred material for the base material 50 is polyether ether ketone (PEEK). In one embodiment of the invention, the sheath 24 extends the entire length of the probe shaft, with the exception of a distal tip of the probe shaft 18. In this manner, an RF ablation electrode 26 is formed by the exposed portion of the distal tip.

Figure 3A:
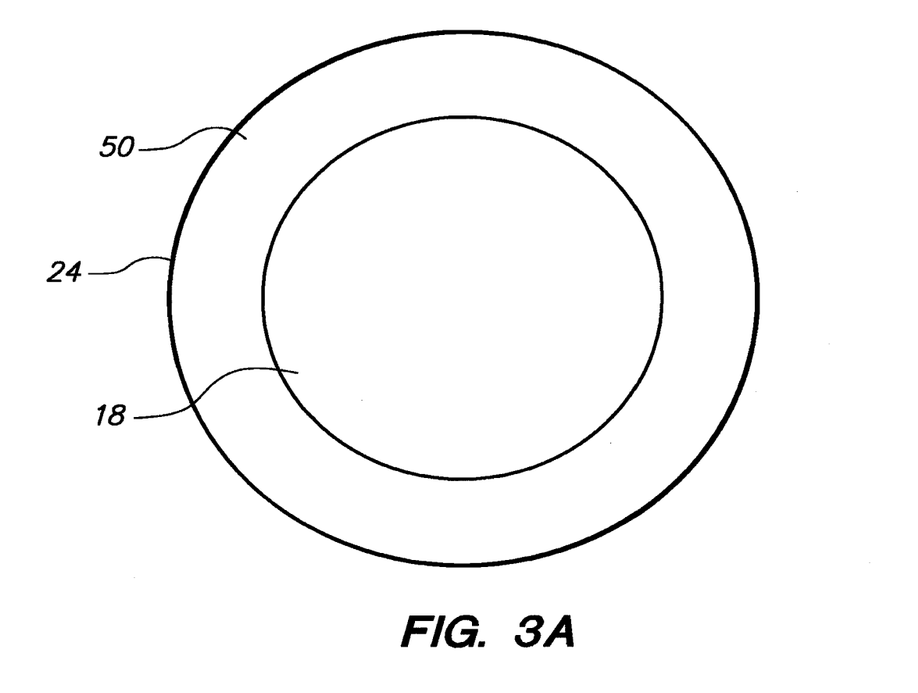
FIGS. 3A-3B illustrate cross-sectional views of the tissue ablation probe of FIG. 2, taken along the line 3-3.
Figure 3B:
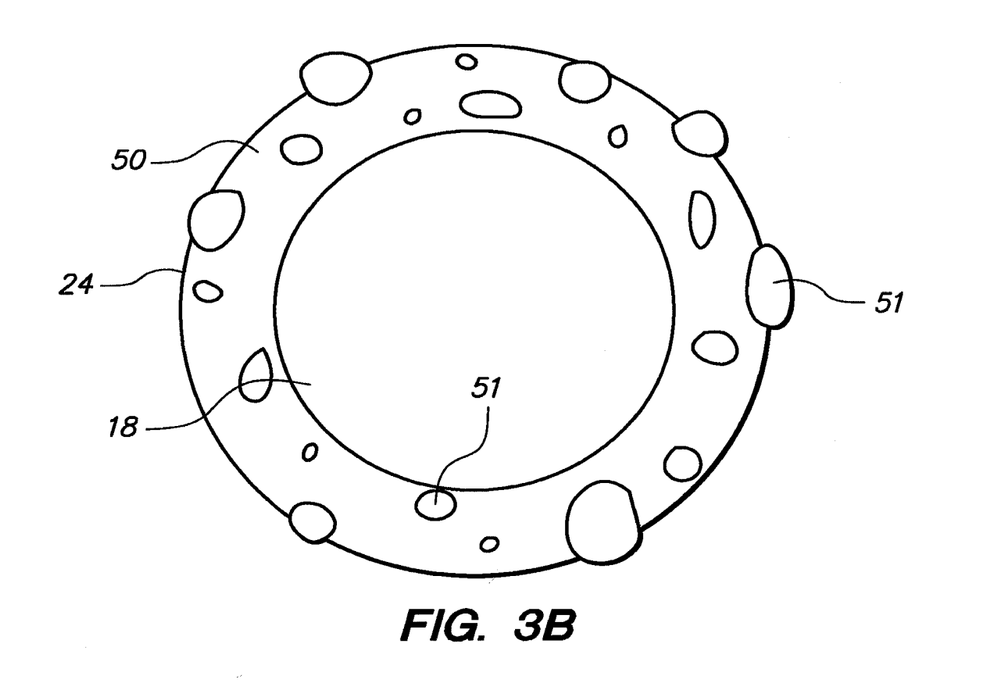

In one embodiment, the sheath 24 may be composed entirely of the base material 50, in particular PEEK, as shown in FIG. 3A. Preferably, however, the sheath 24 may additionally comprise a second material 51 interspersed throughout the base material 50, as shown in FIG. 3B. Notably, for purposes of illustration, the particle size of the second material 51 is shown as being much greater than the actual size of the particles. The second material 51 has a density that is different from that of the base material 50, such that the sheath 24 varies in density. As shown in FIG. 3B, the addition of the second material 51 may also vary the surface profile of the sheath 24. Thus, it can be appreciated that the presence of the second material 51 causes the echogenicity of the ablation probe 12 to be greater than what would result with the base material 50 alone.

The second material 51 is preferably composed of condensed phase particles, i.e. solid, gel, or liquid particles. Examples of condensed phase particles composing the second material 51 are glass, sand, or crystal particles. Alternatively, the second material 51 may be composed of a gas, although the use of gas particles may decrease the durability of the sheath 24. In this case, it is desirable that the base material 50 be composed of a highly durable and electrically insulative material, such as PEEK, such that the physical integrity of the sheath 24 is maintained. The second material 51 may also be composed of more than one type of particle. For example, the second material 51 may be composed of both glass particles and gel particles.

The second material 51 may be interspersed throughout the base material 50 in uniform or non-uniform portions. Additionally, the second material 51 may be interspersed throughout the base material in a uniform pattern or non-uniform manner. For example, it may be more cost-effective if the second material 51 is produced such that the particles composing the second material 51 vary considerably in size, as opposed to maintaining a narrow size range for the particles. In addition, instead of having the second material 51 added uniformly to the base material 50, it may be more efficient, and cost-effective, to simply mix particles of the second material 51 into the base material 50 such that the second material 51 is randomly dispersed throughout the base material 50 when it is applied to the probe shaft 18.

The distal tip of the probe shaft 18 is a tissue-penetrating tip, which allows the ablation probe 12 to be more easily introduced through tissue, while minimizing tissue trauma. The RF ablation electrode 26 located at the distal tip may be affixed to the distal end 22 of the probe shaft 18, or it may be deployable from the probe shaft 18. The probe shaft 18 is preferably composed of a rigid or semi-rigid material, such that the ablation probe 12 can be introduced through solid tissue to a target tissue site. Alternatively, the ablation probe 12 may be introduced through the tissue with the aid of a cannula and trocar assembly, in which case, the probe shaft 18 may be composed of a flexible material, and the distal end 22 may be blunted.

The ablation probe 12 further comprises a handle 34 mounted to the proximal end 20 of the probe shaft 18. The handle 34 is preferably composed of a durable and rigid material, such as medical grade plastic, and is ergonomically molded to allow a physician to more easily manipulate the ablation probe 12. The handle 34 comprises an electrical connector 36 with which the cable 16 (shown in FIG. 1) mates. Alternatively, the RF cable 16 may be hardwired within the handle 34. The electrical connector 36 is electrically coupled to the ablation electrode 26 via the probe shaft 18, with the insulative sheath 24 operating to focus RF energy at the electrode 26 where the targeted tissue presumably lies.

In the illustrated embodiment, the RF current is delivered to the electrode 26 in a monopolar fashion, which means that current will pass from the electrode 26, which is configured to concentrate the energy flux in order to have an injurious effect on the surrounding tissue, and a dispersive electrode (not shown), which is located remotely from the electrode 26 and has a sufficiently large area (typically 130 $cm^2$ for an adult), so that the current density is low and non-injurious to surrounding tissue. The dispersive electrode may be attached externally to the patient, e.g., using a contact pad placed on the patient's flank.

Referring back to FIG. 1, the RF generator 14 may be a conventional general purpose electrosurgical power supply operating at a frequency in the range from 300 kHz to 9.5 MHz, with a conventional sinusoidal or non-sinusoidal wave form. Such power supplies are available from many commercial suppliers, such as Valleylab, Aspen, Bovie, and Ellman. Most general purpose electrosurgical power supplies, however, are constant current, variable voltage devices and operate at higher voltages and powers than would normally be necessary or suitable. Thus, such power supplies will usually be operated initially at the lower ends of their voltage and power capabilities, with voltage then being increased as necessary to maintain current flow. More suitable power supplies will be capable of supplying an ablation current at a relatively low fixed voltage, typically below 200 V (peak-to-peak). Such low voltage operation permits use of a power supply that will significantly and passively reduce output in response to impedance changes in the target tissue. The output will usually be from 5 W to 300 W, usually having a sinusoidal wave form, but other wave forms would also be acceptable. Power supplies capable of operating within these ranges are available from commercial vendors, such as Boston Scientific Therapeutics Corporation. Preferred power supplies are models RF-2000 and RF-3000, available from Boston Scientific Corporation.

Figure 4:
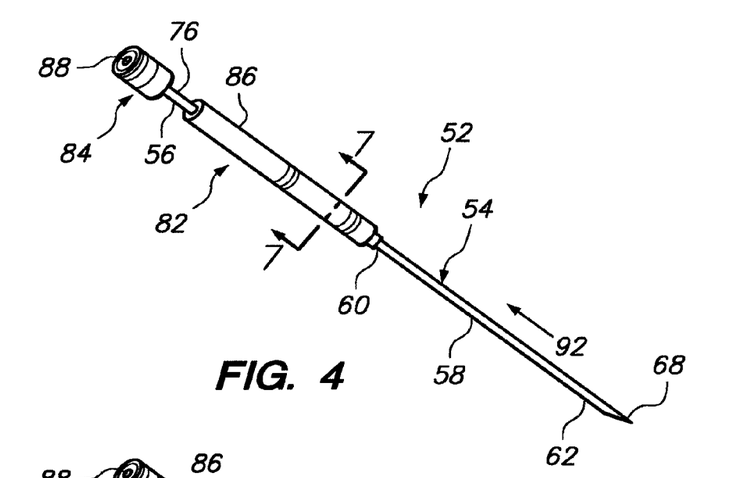
FIG. 4 is a perspective view of another tissue ablation probe that can be used within the tissue ablation system of FIG. 1, wherein an electrode array is particularly shown retracted.
Figure 5:
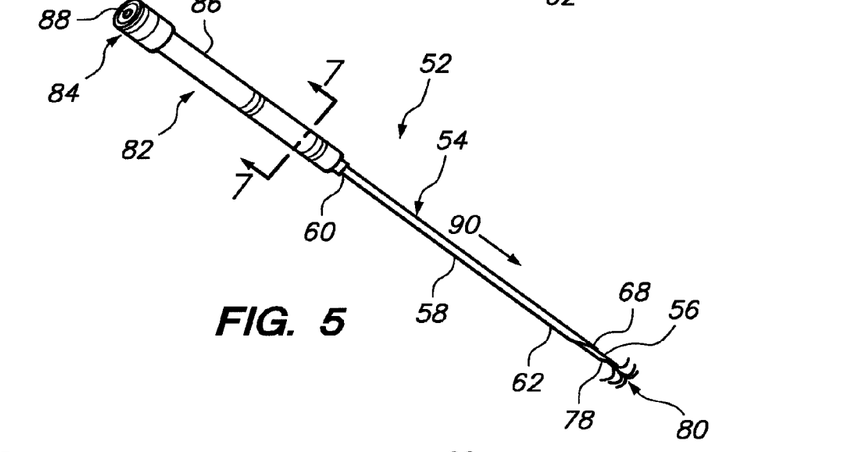
FIG. 5 is a perspective view of the tissue ablation probe of FIG. 4, wherein the electrode array is particularly shown deployed.

Referring now to FIGS. 4 and 5, another tissue ablation probe 52 that can be used in conjunction with the RF generator 14 to create an alternative tissue ablation system will be described. The tissue ablation probe 52 includes an elongated cannula 54 and an inner probe shaft 56 slidably disposed within the cannula 54. The cannula 54 includes an elongate shaft 58 having a proximal end 60, a distal end 62, and a central lumen 64 (shown in FIGS. 6A-6B), and an electrically insulative sheath 66 (shown in FIGS. 6A-6B) disposed on the cannula shaft 58.

The cannula shaft 58, itself, is composed of an electrically conductive material, such as stainless steel. The material from which the cannula shaft 58 is composed is preferably a rigid or semi-rigid material, such that the ablation probe 52 can be introduced through solid tissue to a target tissue site. The distal end 62 of the cannula shaft 58 comprises a tissue-penetrating tip 68, which allows the ablation probe 52 to be more easily introduced through tissue, while minimizing tissue trauma. Alternatively, the ablation probe 52 may be introduced through the tissue with the aid of another cannula and trocar assembly, in which case, the cannula shaft 58 may be composed of a flexible material, and the distal end 62 may be blunted. The cannula shaft 58 has a suitable length, typically in the range from 5 cm to 30 cm, preferably from 10 cm to 25 cm, and an outer diameter consistent with its intended use, typically being from 0.7 mm to 5 mm, usually from 1 mm to 4 mm.

Figure 6A:
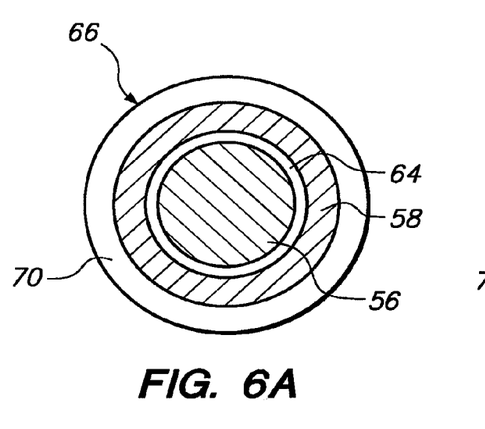
FIGS. 6A-6B illustrate cross-sectional views of the tissue ablation probe of FIGS. 4 and 5, taken along the line 7-7.
Figure 6B:
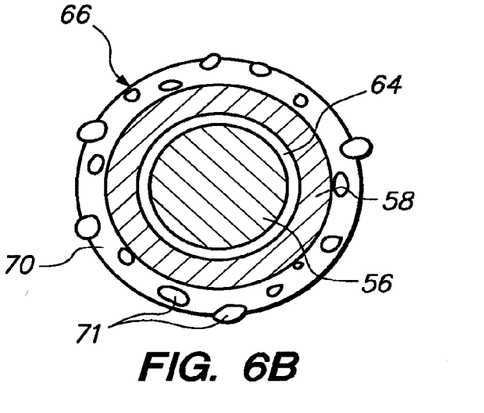

In the illustrated embodiment, the insulative sheath 66 is affixed to the cannula shaft 58, and may be applied to the cannula shaft 58 using any suitable means, e.g., as a heat shrink or extrusion. The insulative sheath 66 has a composition similar to that of the insulative sheath 24 described above. In particular, as best shown in FIGS. 6A-6B, the insulative sheath 66 is composed of a base material 70, in particular PEEK, as shown in FIG. 6A. Preferably, as described earlier in respect to FIGS. 3A and 3B, the sheath 66 additionally comprises a second material 71 interspersed throughout the base material 70, as shown in FIG. 6B. Notably, for purposes of illustration, the particle size of the second material 71 is shown as being much greater than the actual size of the particles. As discussed earlier, the second material 71 has a density that is different from that of the base material 70, such that the sheath 66 varies in density. As shown in FIG. 6B, the addition of the second material 71 may also vary the surface profile of the sheath 66. The base material 70 and the second material 71 provide similar advantages as those discussed above with respect to the base material 50 and the second material 51 in the sheath 24. That is, the base material 70 and the second material 71 increase the echogenicity of the ablation probe 52 such that the probe 52 may be more precisely located using ultrasound imaging.

The inner probe shaft 56 is slidably disposed within the cannula lumen 64 and has a proximal end 76 and a distal end 78, and an array of electrode tines 80 carried by the distal end 78 of the probe shaft 56. Like the cannula shaft 58, the inner probe shaft 56 is composed of an electrically conductive material, such as stainless steel. The inner probe shaft 56 is composed of a suitably rigid material, so that it has the required axial strength to be slide within the cannula lumen 64.

The ablation probe 52 further includes a handle assembly 82, which includes a handle member 84 mounted to the proximal end 76 of the inner probe shaft 56, and a handle sleeve 86 mounted to the proximal end 60 of the cannula 54. The handle member 84 is slidably engaged with the handle sleeve 86 (and the cannula 54). The handle member 84 and handle sleeve 86 can be composed of any suitable rigid material, such as, e.g., metal, plastic, or the like. The handle assembly 82 also includes an electrical connector 88 mounted within the handle member 84. The electrical connector 88 is electrically coupled to the electrode array 80 via the inner probe shaft 56, with the insulative sheath 66 operating to focus RF energy at the electrode array 80 where the targeted tissue presumably lies. The electrical connector 88 is configured for mating with the proximal end of the RF cable 16 (shown in FIG. 1). Alternatively, the RF cable 16 may be hardwired within the handle member 84. Like the previous described ablation probe 52, RF current may be delivered to the electrode array 80 in a monopolar fashion.

It can be appreciated that longitudinal translation of the probe shaft 56 relative to the cannula 54 in a distal direction 90 can be achieved by holding the handle sleeve 86 and displacing the handle member 84 in the distal direction 90, thereby deploying the electrode array 80 from the distal end 62 of the cannula shaft 58 (FIG. 5), and longitudinal translation of the probe shaft 56 relative to the cannula 54 in a proximal direction 92 can be achieved by holding the handle sleeve 86 and displacing the handle member 84 in the proximal direction 92, thereby retracting the probe shaft 56 and the electrode array 80 into the distal end 62 of the cannula 54 (FIG. 4).

Further details regarding electrode array-type probe arrangements are disclosed in U.S. Pat. No. 6,379,353, which is hereby expressly incorporated by reference.

Having described the structure of the tissue ablation system 10, its operation in treating targeted tissue will now be described. The treatment region may be located anywhere in the body where hyperthermic exposure may be beneficial. Most commonly, the treatment region will comprise a solid tumor within an organ of the body, such as the liver, kidney, pancreas, breast, prostrate (not accessed via the urethra), and the like. The volume to be treated will depend on the size of the tumor or other lesion, typically having a total volume from 1 cm$^3$ to 150 cm$^3$, and often from 2 cm$^3$ to 35 cm$^3$. The peripheral dimensions of the treatment region may be regular, e.g., spherical or ellipsoidal, but will more usually be irregular. The treatment region may be identified using conventional imaging techniques capable of elucidating a target tissue, e.g., tumor tissue, such as ultrasonic scanning, magnetic resonance imaging (MRI), computer-assisted tomography (CAT), fluoroscopy, nuclear scanning (using radiolabeled tumor-specific probes), and the like. Preferred is the use of high resolution ultrasound of the tumor or other lesion being treated, either intraoperatively or externally.

Figure 7A:
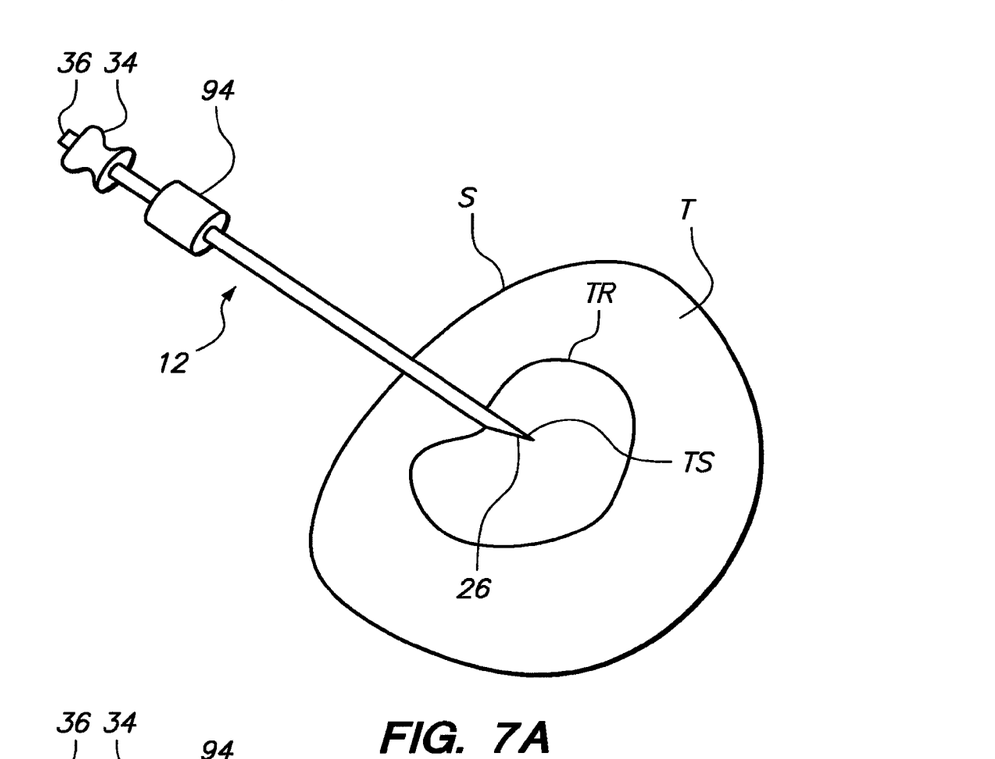
FIGS. 7A-7B illustrate cross-sectional views of one method of using the tissue ablation system of FIG. 1 to treat tissue.
Figure 7B:
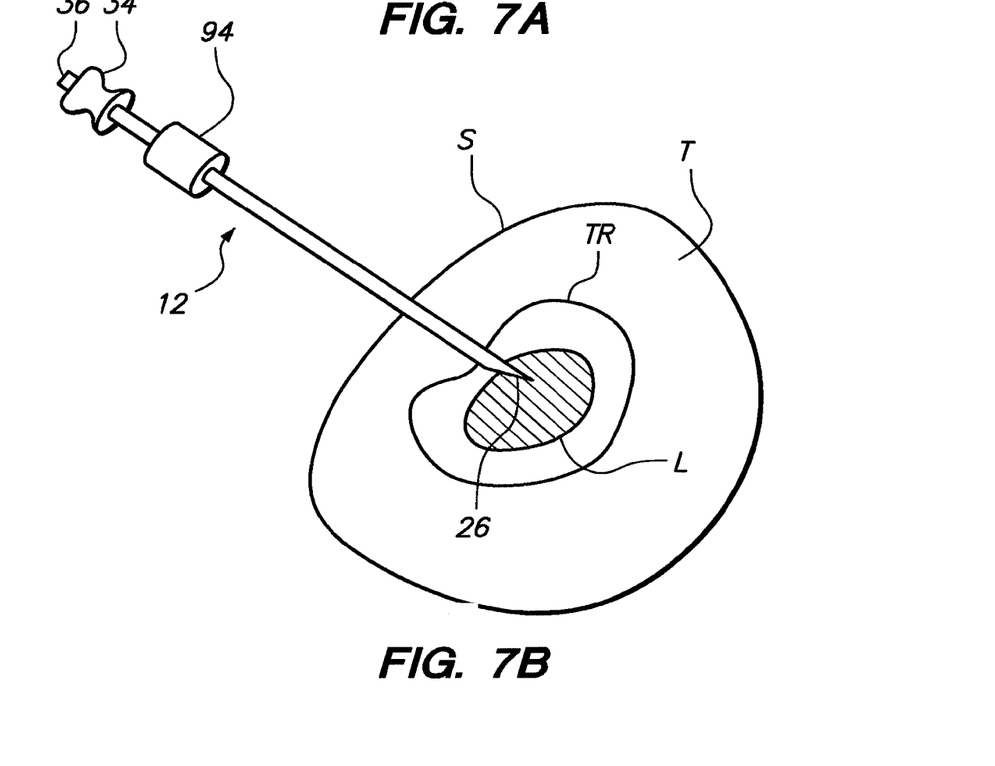

Referring now to FIGS. 7A-7B, the operation of the tissue ablation system 10 is described in treating a treatment region TR with tissue T located beneath the skin or an organ surface S of a patient. The ablation probe 12 is first introduced through the tissue T under the guidance of a conventional ultrasound imaging device, so that the electrode 26 is located at a target site TS within the treatment region TR, as shown in FIG. 7A. This can be accomplished using any one of a variety of techniques. In the preferred method, a delivery device, such as a probe guide 94, is used to guide the ablation probe 12 towards the target site TS. In particular, the probe guide 94 is affixed and aligned relative to the target site TS, and the ablation probe 12 is introduced through the probe guide 94. Facilitated by the sharpened distal tip, the ablation probe 12 is percutaneously introduced through the patient's skin until the electrode 26 is located in the treatment region TR.

As discussed above, the echogenicity of the sheath 24 will allow the user to more precisely locate the ablation probe 12 using ultrasound imaging. This will help to ensure direct contact of the ablation probe 12 with the treatment region and to minimize damage to surrounding healthy tissue.

Once the ablation probe 12 is properly positioned, the cable 16 of the RF generator 14 (shown in FIG. 1) is then connected to the electrical connector 36 of the ablation probe 12, and then operated to transmit RF energy to the electrode 26, thereby ablating the treatment region TR, as illustrated in FIG. 7B. As a result, a lesion L will be created, which will eventually expand to include the entire treatment region TR.

Figure 8A:
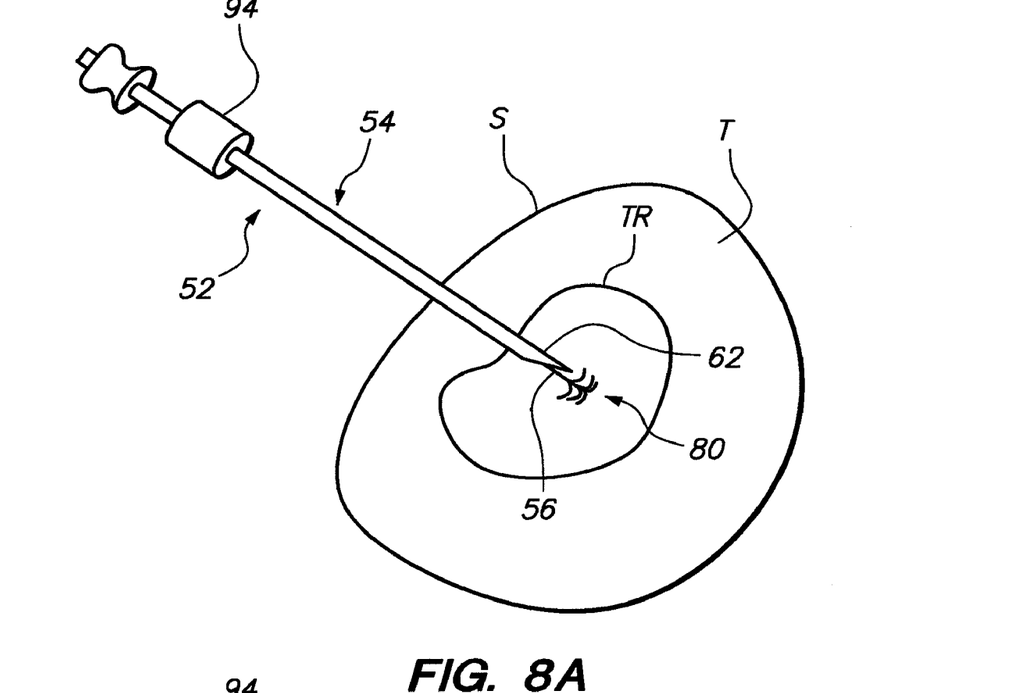
FIGS. 8A-8B illustrate cross-sectional views of another method of using the tissue ablation system of FIG. 1 to treat tissue.

Alternatively, if the ablation probe 52 illustrated in FIGS. 4 and 5 is used, the cannula 54 can be introduced through the probe guide 94 until the distal end 62 of the cannula 54 is located at the target site TS, after which the inner probe shaft 56 can be distally advanced through the cannula 54 to deploy the electrode array 80 out from the distal end 62 of the cannula 54, as shown in FIG. 8A.

Figure 8B:
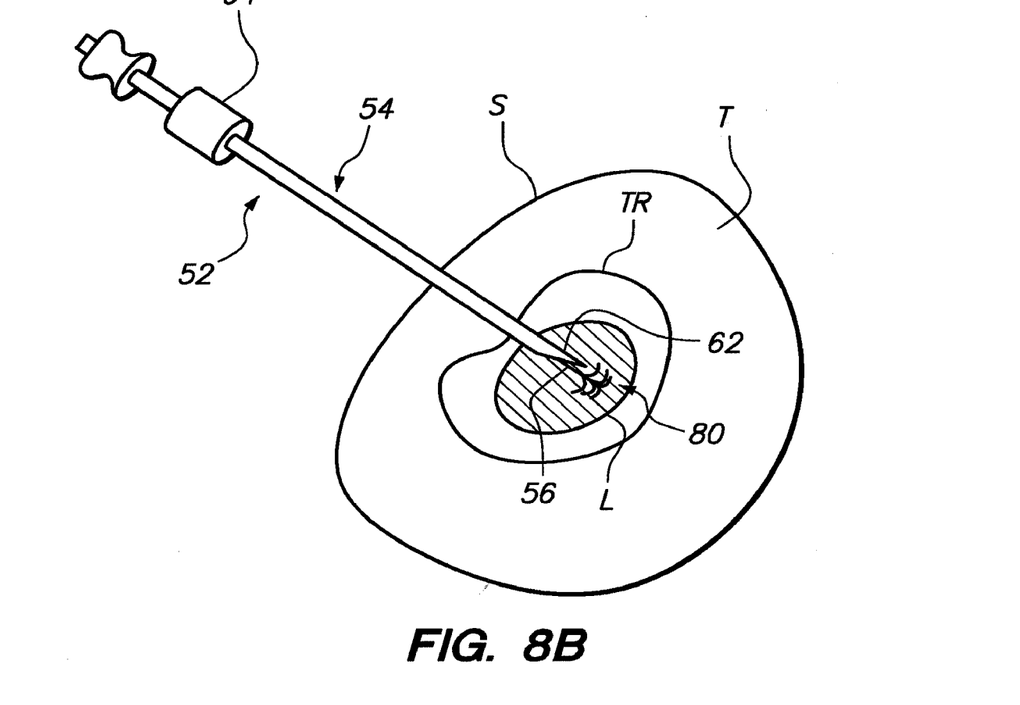

As previously discussed, once the ablation probe 52 is properly positioned, the cable 16 of the RF generator 14 (shown in FIG. 1) is then connected to the electrical connector 88 of the ablation probe 52, and then operated to transmit RF energy to the electrode 26, thereby ablating the treatment region TR, as illustrated in FIG. 8B. As a result, a lesion L will be created, which will eventually expand to include the entire treatment region TR.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

We claim:

1. A tissue ablation probe, comprising:
   an electrically conductive probe shaft having a proximal end and a distal end;
   at least one tissue ablation electrode carried by a distal end of the probe shaft; and
   an electrically insulative outer sheath at least partially comprising polyether ether ketone (PEEK) configured to be slidably disposed over the probe shaft; and
   a plurality of particles distributed through the PEEK, wherein the echogenicity of the tissue ablation probe is increased by the inclusion of the particles.

2. The tissue ablation probe of claim 1, wherein the outer sheath is dimensioned to cover substantially all of the probe shaft.

3. The tissue ablation probe of claim 1, wherein the particles comprise solid particles.

4. The tissue ablation probe of claim 1, wherein the particles comprise liquid particles.

5. The tissue ablation probe of claim 1, wherein the particles comprise gas particles.

6. The tissue ablation probe of claim 1, wherein the particles are interspersed through the outer sheath in a uniform manner.

7. The tissue ablation probe of claim 1, wherein the particles are interspersed through the outer sheath in a non-uniform manner.

8. The tissue ablation probe of claim 1, further comprising a handle having an electrical connector therein disposed at the proximal end of the probe shaft.

9. The tissue ablation probe of claim 8, further comprising a RF generator operatively connected to the probe shaft via the electrical connector.

10. A tissue ablation probe, comprising:
    an electrically conductive elongated cannula having a lumen extending between a proximal end and a distal end;
    a probe shaft having a proximal end and a distal end, the probe shaft being slidably disposed within the lumen of the elongated cannula;
    an electrically insulative outer sheath at least partially comprising polyether ether ketone (PEEK) disposed over the electrically conductive elongated cannula; and
    a plurality of particles distributed through the PEEK, wherein the echogenicity of the tissue ablation probe is increased by the inclusion of the particles.

11. The tissue ablation probe of claim 10, therein the probe shaft comprises a plurality of tines disposed at the distal end thereof.

12. The tissue ablation probe of claim 10, further comprising a handle sleeve mounted to a proximal end of the cannula and a handle member mounted to the proximal end of the probe shaft.

13. The tissue ablation probe of claim 12, further comprising an electrical connector mounted within the handle member.

14. The tissue ablation probe of claim 10, wherein the particles comprise solid particles.

15. The tissue ablation probe of claim 10, wherein the particles comprise liquid particles.

16. The tissue ablation probe of claim 10, wherein the particles comprise gas particles.

17. The tissue ablation probe of claim 10, wherein the particles are interspersed through the outer sheath in a uniform manner.

18. The tissue ablation probe of claim 10, wherein the particles are interspersed through the outer sheath in a non-uniform manner.

19. A method of ablating tissue comprising:
    introducing the tissue ablation probe of claim 1 through a delivery device into a tissue region; and
    ablating the tissue region with the tissue ablation probe.

20. A method of ablating tissue comprising:
    introducing the electrically conductive elongated cannula of claim 10;
    advancing the probe shaft distally through the elongated cannula; and
    ablating the tissue region with the probe shaft.

* * * * *